(12) United States Patent
Kauling et al.

(10) Patent No.: US 8,328,167 B2
(45) Date of Patent: Dec. 11, 2012

(54) MODULES FOR MEMBRANE AERATION

(75) Inventors: Jörg Kauling, Köln (DE); Hans-Jürgen Henzler, Solingen (DE); Sebastian Schmidt, Haan (DE); Helmut Brod, Köln (DE); Klaus Kaiser, Bergisch Gladbach (DE); Stephan Kirchner, Wuppertal (DE); Dirk Havekost, Köln (DE)

(73) Assignee: Bayer Technology Services GmbH, Leverkusen (DE)

( * ) Notice: Subject to any disclaimer, the term of this patent is extended or adjusted under 35 U.S.C. 154(b) by 838 days.

(21) Appl. No.: 12/084,418

(22) PCT Filed: Oct. 25, 2006

(86) PCT No.: PCT/EP2006/010263
§ 371 (c)(1),
(2), (4) Date: Sep. 17, 2008

(87) PCT Pub. No.: WO2007/051551
PCT Pub. Date: May 10, 2007

(65) Prior Publication Data
US 2009/0286318 A1 Nov. 19, 2009

(30) Foreign Application Priority Data
Nov. 7, 2005 (DE) .......................... 10 2005 053 334

(51) Int. Cl.
*B01F 3/04* (2006.01)
(52) U.S. Cl. ..................... 261/93; 261/122.1; 435/297.4
(58) Field of Classification Search ................... 261/93, 261/122.1, 124; 435/296.1, 297.1, 297.4
See application file for complete search history.

(56) References Cited

U.S. PATENT DOCUMENTS

| | | | |
|---|---|---|---|
| 4,075,100 A * | 2/1978 | Furuta et al. .................. 210/266 |
| 4,647,539 A * | 3/1987 | Bach .......................... 435/297.4 |
| 4,649,114 A * | 3/1987 | Miltenburger et al. ........ 435/401 |
| 4,870,018 A | 9/1989 | Lehmann |
| 5,110,741 A | 5/1992 | Ohi et al. |
| 5,443,985 A | 8/1995 | Lu et al. |
| 6,001,585 A | 12/1999 | Gramer |
| 2004/0229343 A1 * | 11/2004 | Husain et al. ................. 435/262 |

FOREIGN PATENT DOCUMENTS

| | | |
|---|---|---|
| DE | 38 09 163 | 9/1988 |
| DE | 195 28 871 | 2/1996 |
| DE | 195 37 033 | 8/1996 |
| EP | 0 172 478 | 2/1986 |
| EP | 0 727 481 | 8/1996 |
| JP | 2-249478 A * | 10/1990 .............. 435/297.4 |
| WO | 87/02054 | 4/1987 |
| WO | 94/11094 | 5/1994 |
| WO | 02/31108 | 4/2002 |
| WO | 03/020919 | 3/2003 |
| WO | 2004/071973 | 8/2004 |

OTHER PUBLICATIONS

International Search Report mailed Feb. 15, 2007 for International Application No. PCT/EP2006/010263.
H. J. Henzler and D. J. Kauling, "Oxygenation of Cell Cultures", Bioprocess Engineering, Springer-Verlag, Wuppertal, Germany, 1993, pp. 61-75.
Dirk Nehring et al., "Experimental Study of a Ceramic Microsparging Aeration System in a Pilot-Scale Animal Cell Culture", Biotechnology Progress, 2004, 20, pp. 1710-1717.
Hanshi Qi, Goran Jovanoic, James Michaels and Konstantin Konstantinov, Animal Cell Technology: From Target to Market, "The Art & Science of Micro-Sparging in High-Density Perfusion Cultures of Animal Cells", Proceedings of the 17th ESACT Meeting Tylösand, Sweden, Jun. 10-14, 2001, pp. 412-415.
Janine T. Bohlmann, "Development of a Novel Ramjet Membrane Reactor for Cell Culture Technology Using CFD", CIT, No. 75, 2003, pp. 131-135 w/translation.

* cited by examiner

*Primary Examiner* — Richard L Chiesa
(74) *Attorney, Agent, or Firm* — Wenderoth, Lind & Ponack, L.L.P.

(57) ABSTRACT

The present invention relates to a device for the aeration of liquid media by tube aeration, special tube modules contained therein and the use of a device for the aeration of liquid media.

20 Claims, 5 Drawing Sheets

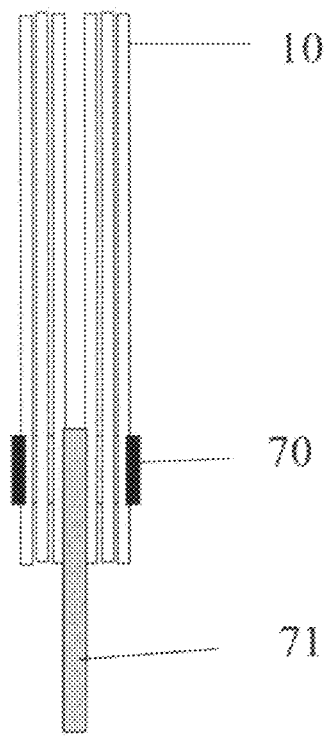
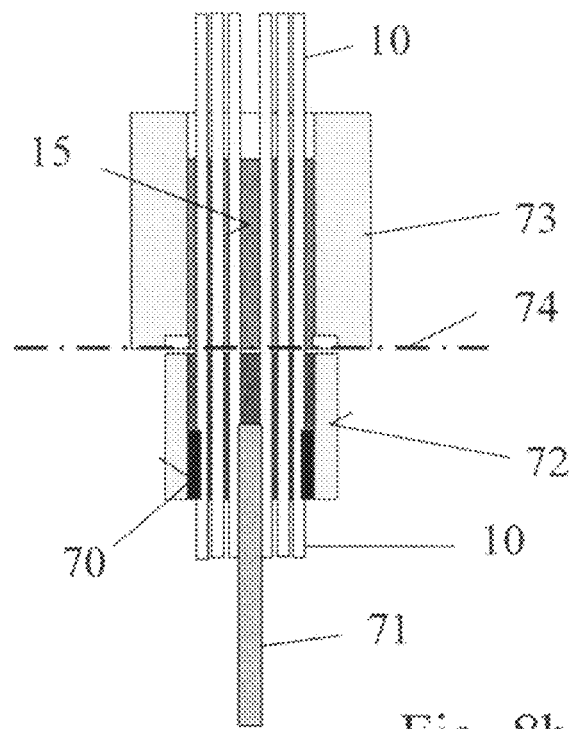
Fig. 8a
Fig. 8b

MODULES FOR MEMBRANE AERATION

This application is a national stage of International Application No. PCT/EP2006/010263, filed on Oct. 25, 2006.

BACKGROUND OF THE INVENTION

I. Technical Field

The present invention relates to a device for the aeration of liquid media by means of tube aeration, special tube modules contained therein and the use of a device for the aeration of liquid media.

II. Description of the Related Art

In the pharmaceuticals industry, the production of recombinant proteins is becoming ever more important. On account of its capabilities in producing glycosylated proteins with posttranslational modifications, animal cell culture has become well-established for the production of more complex proteins.

Usually intensive bubble aeration with dispersing stirring elements is used for supplying oxygen to microorganisms.

Animal cells impose special requirements on the technical reactors in which they are cultivated. High shearing forces, as are necessary for dividing up gas bubbles, are to be avoided in particular, since they irreversibly damage the cell membranes of the cells without cell walls and consequently have disadvantageous consequences for the growth of the cell cultures.

Apart from during dispersion by the stirring element, shearing forces are also released during the formation and bursting of the gas bubbles on the surface of the liquid. Bubble aeration can therefore only take place in cell cultivation with very low throughputs of gas. The stiffing element in this case does not undertake any gas bubble dispersing function but essentially only a distributing function. Therefore, in the case of cells that are sensitive to shearing, an adequate supply of oxygen can only be ensured to relatively low cell densities by an aeration method that uses large bubbles. (H. J. Henzler: "Verfahrenstechnische Auslegungsunterlagen für Rührbehäter als Fermenter" [process engineering design documents for stirring tanks as fermenters) Chem. Ing. Tech. 54 (1982) No. 5 pages 461-476, H. J. Henzler, J. Kauling: "Oxygenation of cell cultures" Bioprocess Engineering 9 (1993) pages 61-75, "Mischen and Rühren" [mixing and stirring] by M. Kraume, WILEY-VCH 2003)

To improve the oxygen supply, the use of sintered aerators of metallic or ceramic materials with pore widths of up to 0.2 µm has been proposed, allowing small bubbles to be produced with little shearing. (D. Nehring, P. Czermak, J. Vorlop, H. Lübben: "Experimental study of a ceramic micro sparging aeration system in a pilot scale animal cell culture" Biotechnology Progress 20 (2004)6, pages 1710-1717, Hanshi, Qi, Konstantin Konstantiniov: "The Art & Science of Micro-Sparging in High-Density Perfusion Cultures of Animal Cells" 17th ESTAC meeting, Tylosand, Sweden, 2001). However, when used over a long time, the sintered aerators have a tendency to become clogged. Furthermore, foaming problems may occur, requiring the use of anti-foaming agents, which in turn may lead to losses in yield in the reprocessing.

A low-shear method of supplying oxygen is represented by membrane aeration, in which the oxygen passes a membrane wall stretched between the gas phase and the culture medium. Such membranes can be wound up as tubes on cylindrical cage stators. (H. J. Henzler, J. Kauling: "Oxygenation of cell cultures" Bioprocess Engineering 9 (1993) pages 61-75, EP A1 0172478, WO A1 87/02054). To accommodate large exchange areas, the tubes are placed close together with as little spacing as possible.

The spacing S between the tubes, referred to the outside diameter of the tube D, is generally in the range of 0<S/D<1 in the case of suspended cells. If cells immobilized on carrier materials are used, greater spacings may also be advisable to ensure the permeability of the tube matrix with respect to the carrier particles. Both vertically and horizontally wound stators are used. Vertical winding is to be preferred in principle to prevent deposits on the tubes. Furthermore, in this way virtually double the tube area can be placed in the reactor. With the aid of low-shear radially transporting stirring elements such as blade or anchor stirrers, the concentrically arranged tube membranes are flowed through in the radial direction, in order to minimize the mass transfer resistance on the liquid side.

Other reactors, known as hollow-fiber reactors, connected in circular flow to a stirred tank reactor, are flowed through by medium (DE 195 37 033 A1, EP 0727 481 A2, DE 195 28 871 C2, U.S. Pat. No. 6,001,585 A, U.S. Pat. No. 5,443,985 A, WO 02/31108 A1). Here it is necessary for the culture solution to be constantly pumped around between the stirred tank reactor, in which the supply of media and the pH adjustment take place, and the aeration reactor. To be able to realize a high mass transfer, the mass transfer resistance on the liquid side at the membranes must be reduced, which requires high pumping circulation rates and consequently causes shearing problems. A further variant is the reciprocating jet reactor, in which the membrane areas are moved in an oscillating manner in the vertical direction. (Janine T. Bohlmann: "Entwicklung eines neuartigen Staustrahl-Membranreaktors für die Zellkulturtechnik mittels CFD" [development of a novel ramjet membrane reactor for cell culture technology by means of CFD] CIT, No. 75 (2003) pages 131-135). With such a configuration on an industrial scale, problems in handling the complicated membrane stator are likely, as well as technical problems in providing sterile conditions due to the sealing of the axial bearings. For the reasons stated, wound tube stators subjected to the flow of a coaxially arranged stirrer still appear to be the most technically sophisticated and reliable solution.

Silicone has been widely adopted in favor of porous polymers as the tube material. Reasons for this are the high gas permeability, the high thermal resistance and the tube properties distributed homogeneously over the length of the tube segments of over 50 m, properties that are even retained after sterilization. The great tube lengths of the tube segments serve for shortening the time-intensive production of the coaxial tube stators. The silicone tube is generally discarded after it has been used once, so that the considerable effort involved in producing an aeration cage is required each time after fermentation. The advantage of a less labor-intensive solution achieved by the use of long tube segments is also offset by disadvantages, however. For instance, compliance with an upper pressure loss limit for fixing the tube to distribution systems requires the use of large tube diameters in order to limit the pressure drop in the tube segments that is proportionately dependent on the ratio of tube length to tube diameter. Larger tube diameters in turn lead to a strength-dependent increase in the wall thickness, which causes a proportionate increase in the diffusion resistance in the mass transfer through the tube. A further considerable problem is represented by the reproducibility of the tube winding, which depends on the expenditure of force in stretching the tube, which cannot be definitively determined. In the case of vertical winding, a winding that is too tight leads to a cross-sectional restriction at the points of deflection and to a change in the pressure profile over the length of the tube. With tubes that are insufficiently stretched, there is the risk of the tubes being damaged by contact with the stirring element. A fundamental problem of membrane aeration is represented by the scaling of the specific tube surface area A/V, which decreases with the reactor volume $V^{1/3}$, putting an upper limit on the scale of fermentation. It is not possible to compensate for this disadvantage by changed hydrodynamic conditions in the fermenter, for example by subjecting the tubes to improved flow with increased circumferential stirrer velocity, because of the increasing shear loading and the additional diffusion resistance, which cannot be hydrodynamically influenced.

SUMMARY OF THE INVENTION

On the basis of the prior art, the object is now to avoid these disadvantages that are known for wound tube stators and other membrane aeration systems from the prior art.

This object is achieved surprisingly easily by the device according to the invention, comprising at least one tube module according to the invention and corresponding mountings.

Consequently, a tube module and a corresponding device for aerating a liquid medium, comprising a mounting and at least one associated tube module, are the subject of the present application.

The corresponding tube module, characterized by the combination of a number of pieces of tube aligned in parallel in a head mounting and a foot mounting, also referred to as head pieces of the tube module or tube module head (pieces), which can be connected by suitable connections to a mounting regulating the supply and removal of gas, is the subject of this application.

The pieces of tube processed in the tube module according to the invention are short, with preference having in the restrained state a length of 1-2 times the stator height. The stator height H, referred to the tank diameter D, is approximately $0.5<H/D<5$, a range of $0.8<H/D$ 3 being preferred and an H/D ratio of 2 being particularly preferred. For the backflow of the fluid from the edge of the tank into the center of the reactor, an adequate distance of the stator from the surface of the liquid and from the bottom of the reactor is required. This distance is dependent on the hydrodynamic transporting conditions and is favorably between 2% and 20% of the filling height.

The pieces of tube processed in the tube module according to the invention are usually fixed in a gas-tight manner in the head and foot pieces at both ends of the tube, with preference by cementing in place with a suitable adhesive, with particular preference with 2-component adhesive or silicone adhesives; suitable for example are commercially available silicone sealing compounds which cure to form an elastomeric silicone polymer and have the quality required by the FDA for pharmaceutical processes and thermal resistance up to 134° C., for example the RTV 8001 system from GE Bayer Silicones.

The outside diameter of the pieces of tube processed according to the invention is usually 0.1-10 mm, with preference 0.5 to 3 mm.

The wall thicknesses of the pieces of tube processed according to the invention are usually between 0.05 and 2, with preference between 0.1 and 0.5 mm.

The pieces of tube are fitted in vertically stretched parallel sheets of one or more layers, the parallel alignment being accomplished by adhesive strips behind the tube module head piece or with preference the cast tube module head piece itself (see for example FIGS. 3 and 4, elements (12)/(22)-(11)/(23)-(11)/(21)-(12)/(20) or FIG. 9a, FIG. 9b and FIG. 9c, element (91)).

The tube modules and the mounting, with preference a ring stator, when put together produce a device that combines the stator and aeration effect in one unit and is likewise the subject of this application.

In the operating state in a corresponding reactor/fermenter, the device according to the invention is subjected to the flow of a coaxially arranged stirring element, which ensures adequately thorough mixing of the medium.

The tube module head pieces of the tube modules are connected to the mounting by means of connecting elements, to make it possible for the aeration medium to be led in and away. Such connecting elements between the tube module head and the mounting are, for example, tube or screw connections, tube couplings or, favorably, locking-in elements. In the case of tube connections, there is, for example, the possibility of using a further adhesive bonding step to make the tube module head have a tubular attachment, with which the tube module can be easily pulled onto a hose connection provided by the stator. If tube couplings are used, the tube module head is cemented in place in one of the two coupling pieces. In spite of the somewhat higher costs, it is recommendable from a maintenance point of view to use the more sensitive coupling version for the production of the aeration modules designed as disposable articles and to install the more simple counterpart, the more robust coupling nipple, in the stator. A non-positive connection to the supply element is established with particular preference by means of locking-in elements provided on the tube module head, sealing of the tube module and the supply element from the outside space being made possible by means of surface pressure on the silicon surface cast into the tube module head.

In a preferred embodiment, the overall device comprises a respective supply station with connections for the supply and removal of gas for the coupling of the tube module heads.

In a particularly preferred embodiment, the supply stations for the supply and removal of gas are segmented, so that regions of different pressure levels can be set up for the separate optimization of oxygen and carbon dioxide supply and disposal. In this case, each segment comprises a connection of its own for the supply and removal of gas.

Particularly preferred as the mounting is a stator construction in which the gas supply and disposal stations are accommodated together in the upper region of the reactor, the tubes being deflected by 180° between the stations by an opposite deflecting device.

Particularly preferred in addition are devices with a device which prevents the tubes from being drawn in by the stirring element.

The tubes of the tube modules according to the invention consist of a gas-permeable plastic; the gas-permeable and thermally stable silicone membranes known from the prior art are preferred.

BRIEF DESCRIPTION OF THE DRAWINGS

The present invention is explained with the aid of FIGS. 1 to 9, without being restricted to these.

FIG. 8 shows the production of a tube module, winding of a tube mat on piece of the tube (FIG. 8a), filling of a module head via piece of the tube (FIG. 8b).

DETAILED DESCRIPTION OF THE INVENTION

Figure 9A:
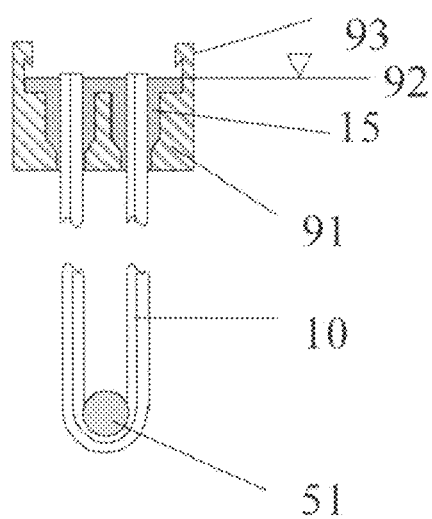
FIG. 9 shows a multi-layer aeration module that can be supplied on one side, with both ends of the tube being received in a single tube module head, a side view of the reception of the ends of the tube and the tube deflection (FIG. 9a), a plan view of tube head module (FIG. 9b) and module connection to a one-side supply station by means of locking-in elements (FIG. 9c).
Figure 9B:
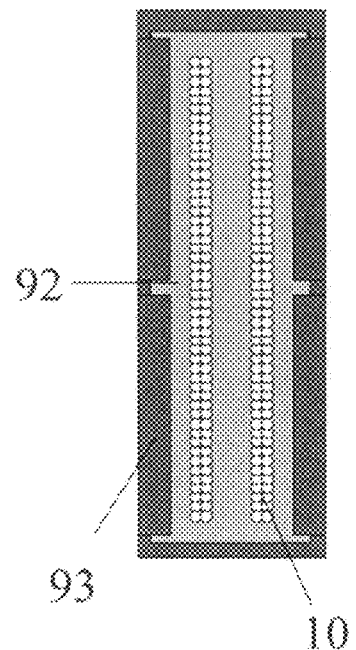
Figure 9C:
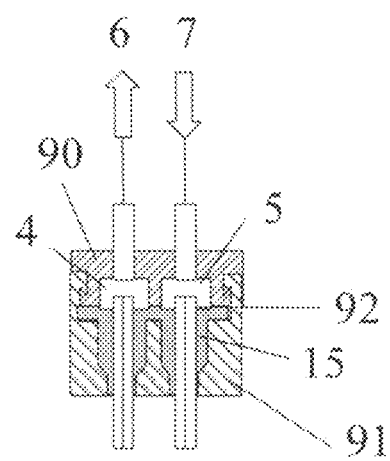

The tube modules can be produced, for example, as follows:

Firstly, the tubes wound up on reels are wound closely to one another in parallel sheets with the same tension as far as possible onto a winding stator rotated as uniformly as possible. The tension of the tubes can be predetermined with moderate accuracy by the weight of an idler pulley that is as stable as possible in its vertical position (forces of acceleration). The circumference of the winding stator is dimensioned such that it corresponds to the length of the restrained tube modules plus a loss from offcuts. The size of the loss from offcuts is caused mainly by differences in tension when winding up the tubes onto the winding stator and is between 10 and 30%, depending on the uniformity of the winding-up operation. After the winding-up operation, the tubes are connected to one another by a thin strip of silicone of about 1-5 mm in thickness and with a width of about 5-20 mm. The strip may be applied without any great accuracy requirements with a trowel, with which the silicone compound—suitable for example are commercially available silicone sealing compounds which cure to form an elastomeric silicone polymer and have the quality required by the FDA for pharmaceutical processes and thermal resistance up to 134° C., for example the RTV 8001 system from GE Bayer Silicones—can be pressed into the spaces between the tubes. After curing, the tubes are cut through at 90° counter to the direction of winding along the strip of silicone. The strip of silicone is for its part subsequently cut to the desired width parallel to the tubes that are to be combined to form the tube module. The desired tube length is obtained from the distance between the tube module heads less a differential length for producing the tension of the moderately restrained module tubes. For the final fixing of the tubes laid out to form parallel sheets, at least one further strip of silicone is provided for fixing the opposite end of the tube. With a deflection of the tubes by means of a deflecting device, it is recommendable to fix the tubes in this region with a further strip. Apart from the parallel alignment of the tubes, this provides the advantage of mechanically protecting the tubes that are more sensitive in the case of the preferred small wall thicknesses from contact. The use of further fixing strips for parallel alignment is not recommended, since they lead to a reduction in the oxygenation. For the adhesive bonding of the tubes in the tube module head pieces, the module sheets may be rolled up, as shown in FIG. 8 a and FIG. 8 b, in the region of the ends of the tube along the strip of silicone (70) onto a stable cylindrical carrier, for example a tube (71), the inside diameter of which is dimensioned such that it is possible to add the highly viscous silicone adhesive compound. The rolled-up tube bundle is introduced into a ring holder (72) in a sealing manner with respect to the strip of silicone (70). The ring holder (72) and the headspace (73) are brought together and the adhesive compound (15) is injected from below into the vertically suspended tube module. After the curing, the ring holder is pulled off a few millimeters from the tube module head and cut with a knife directly behind it along the line (74). A further version of the tubes is shown in FIGS. 9a, 9b and 9c. As represented in FIG. 9a and FIG. 9b, both ends of the tubes (10) that have been wound and connected by the strips of silicone to form mats are cemented in place with the silicone adhesive compound (15) in a single tube module head (91) in such a way that a silicone surface (92) that is exactly defined in height is obtained within the tube module head (91). As FIG. 9c shows, after the curing, the tube module head may be connected non-positively, for example by means of the locking-in elements (93), to a supply element (90), formed as a counterpart. As a result, the silicone surface (92) is pressed in the region of the contact areas toward the supply element (90) in such a way that the channels (4) and (5) of the supply element (=supply line) are sealed with respect to each other and with respect to the outside space. As shown in FIGS. 9 a, b and c, the tube module heads (91) and supply elements (90) may be used in a straight form or in a bent form, which is preferred for installation in a round aeration stator.

Figure 3:
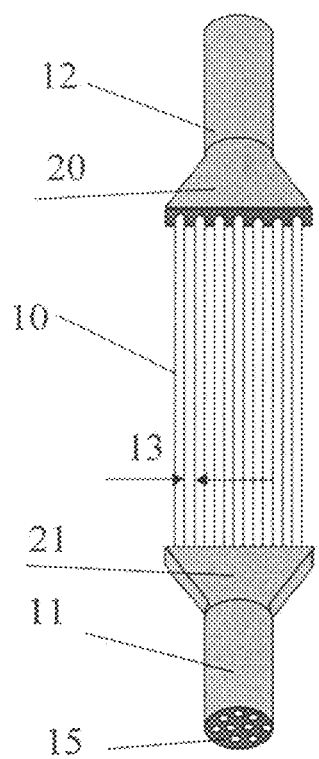
FIG. 3 shows a single-layer membrane module.
Figure 3:
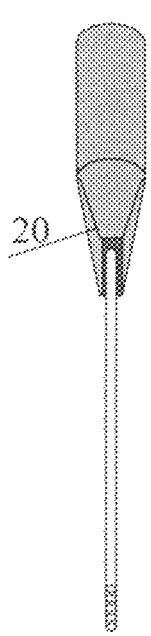

By analogy with WO 03/020919 A2, page 4, lines 23-26, page 29, lines 22-28, page 30, lines 28-31 and page 31, line 1 as well as Annex, page 3, FIG. 3, the tubes of the tube modules are mounted in the reactor by means of annular mountings, which are connected to one another by vertical struts to form a ring stator, which is usually produced completely from high-grade steel. Delimiting itself from this prior art, the ring stator according to the invention serves as an installation and supply device for the tube modules and is equipped for this purpose with the necessary connections for the supply and removal of gas. Furthermore, the mountings offer connections for receiving tube modules. In the case of a preferred embodiment, after being fitted with modules, the stator is set up on the bottom of the reactor by means of spacers and is additionally aligned centrally with 3 to 4 lateral spacers provided on at least two levels. An exact alignment with respect to the stirrer is absolutely necessary to avoid later damage to the tubes by the stirring blades passing by them at a small distance. The connections for the supply and removal of gas can be established after setting up the stator in a simple way by tube lines within the fermenter, for which purpose the ring stator is made with corresponding connection pieces, for example hose connections. A firm anchorage of the ring stator in the fermenter cover, which can be removed for installation, is likewise possible by means of at least 2, preferably at least 3, anchoring points. In this case, the connections can be led out in a sterile manner through the cover into the non-sterile region on the outside and be used as lines for gas supply and disposal.

For reasons of weight and because of the precision required in the introduction into the reactor space to avoid tube damage, fixed suspension of the ring stator and the stirring element in the cover is only recommendable in the case of relatively small reactors. Therefore, above a capacity of 100 L, use of the ring stator mounted on the bottom, and similarly a stirring element mounted on the bottom, is recommended.

In comparison with wound stators, much easier coverage of the stator as well as a considerable increase in the mass transfer can be achieved according to the invention by the use of the tube modules according to the invention, in which parallel aeration tubes are attached at both ends in a mounting that regulates the amount of gas led in and away.

Figure 1:
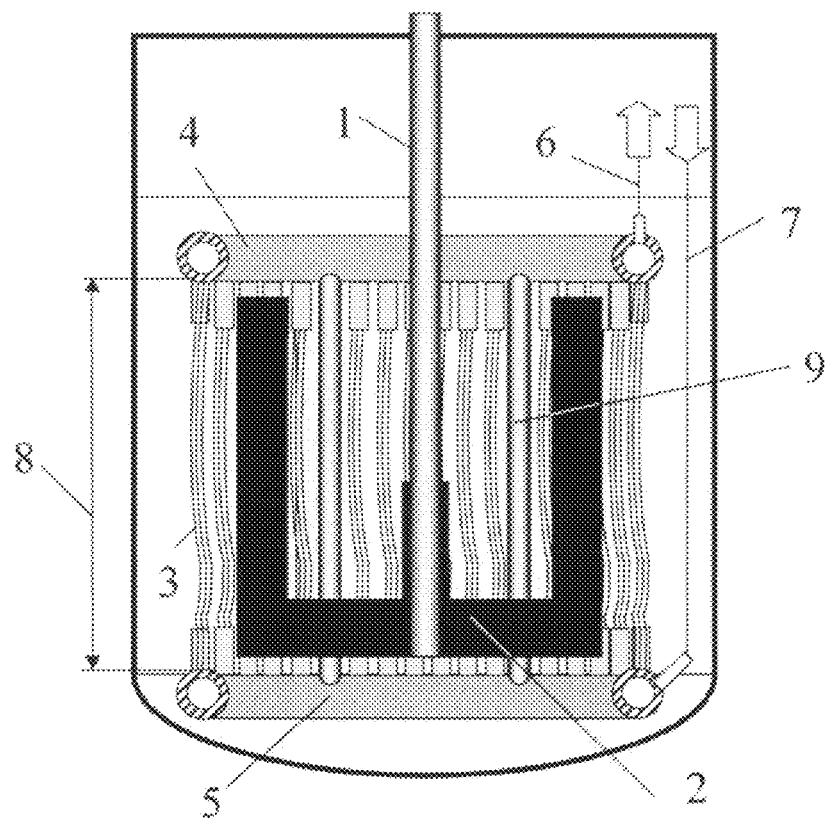
FIG. 1 shows a reactor with membrane modules.

In FIG. 1, tube modules (3) are shown by way of example of modules designed according to the invention. To allow them to be used, the tube modules (3) are connected to the annular supply line (4) and (5) for gas supply and disposal, which can be connected, for example by the connecting elements (9), to form an aeration stator. In the case of the tube modules (3), short pieces of tube with a length of at least once, but with preference twice, the stator height (8) are used according to the invention instead of long tube segments.

Figure 2:
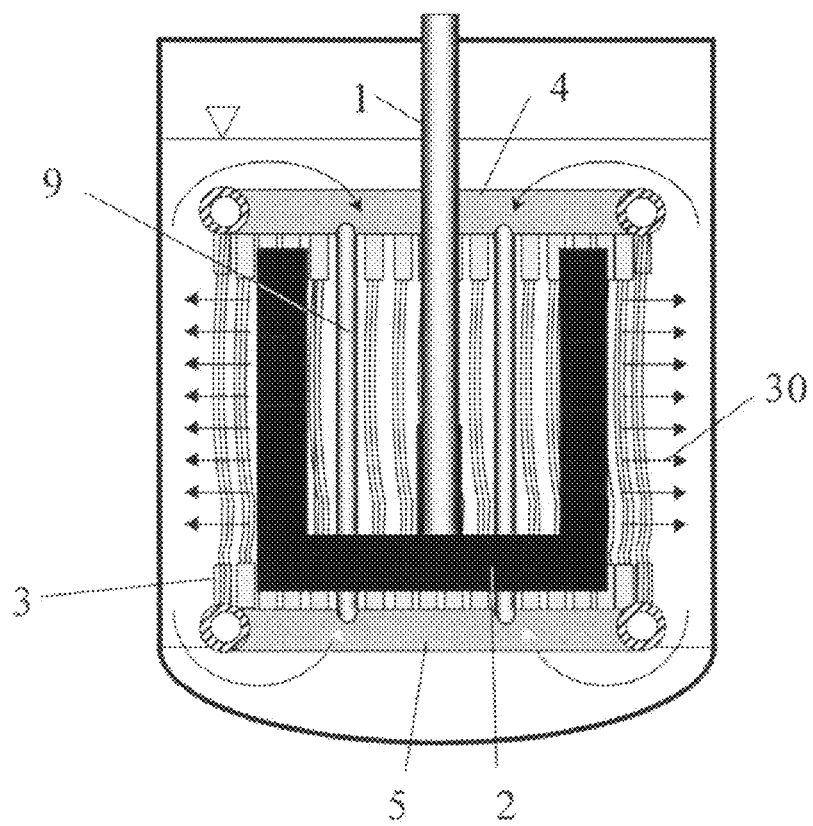
FIG. 2 shows a flow to which the module membranes are subjected.

Comparable to the wound tube stator, the tubes (10) that are restrained in the aeration stator and combined to form tube modules (see FIGS. 3 and 4) can be subjected to the flow (see FIG. 2) in a radial direction (30) of the fermentation medium of a low-shear stirrer (2), with preference an anchor stirrer, arranged coaxially on the stirring shaft (1). To produce the tube modules, as FIG. 3 shows, the pieces of tube are set in a sealed manner at both ends in the tube module heads (11) and (12). The setting may take place, for example, by casting them in an adhesive. Two-component polymer- or silicone-based adhesives, which are commercially available for pharmaceutical processes with the required FDA quality and thermal resistance of up to 134° C. may be used as adhesive (15).

Figure 4:
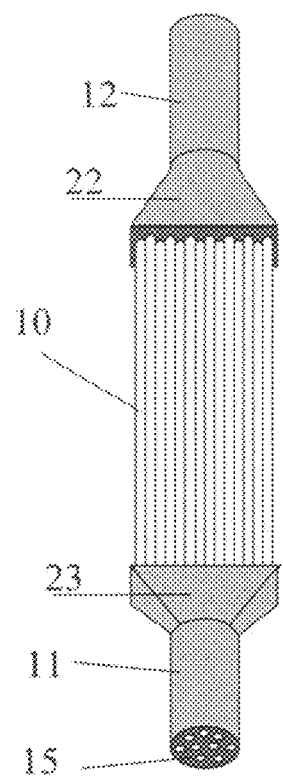
FIG. 4 shows a multi-layer membrane module.
Figure 4:
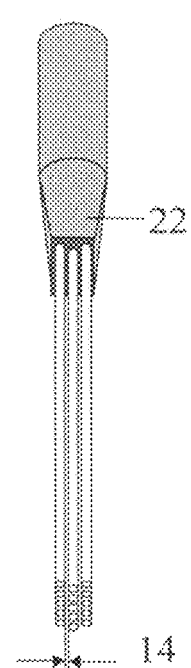

To ensure the optimum function of the membrane aerators, maintenance of a defined porosity of the tube matrix that is flowed through by the medium is absolutely necessary. For this purpose, it is necessary to align the piece of tube into parallel rows of tubes. The mouthpieces (20), (21), (22) and (23) shown in FIG. 3 and FIG. 4 may be used for the parallel alignment of the tubes. This function is, however, also performed comparatively well just by attaching a simple adhesive strip in the vicinity of the tube module heads (11) and (12). The arrangement of the tubes (10) may be of a single-layer form, in one single layer (see FIG. 3), or else, to increase the surface area, in a multi-layer form, in a number of parallel layers, as shown in FIG. 4. The diameters of the tubes (10), which because of the thermal resistance and the FDA-approved products available on the market consist with preference of the material silicone, should lie between 0.1 and 5 mm. Used with preference, however, are small tube diameters from diameters of 0.7 mm, which, with a wall thickness of less than or equal to 0.1 mm, have strengths comparable to tubes with an outside diameter of 3 mm and a wall thickness of 0.5 mm, but on the other hand make possible a transmembrane mass transfer that is improved fivefold.

There are numerous possibilities for the gas-tight fixing of the tube module heads (11) and (12) to the supply line for the gas supply lines (4) and (5).

Figure 5:
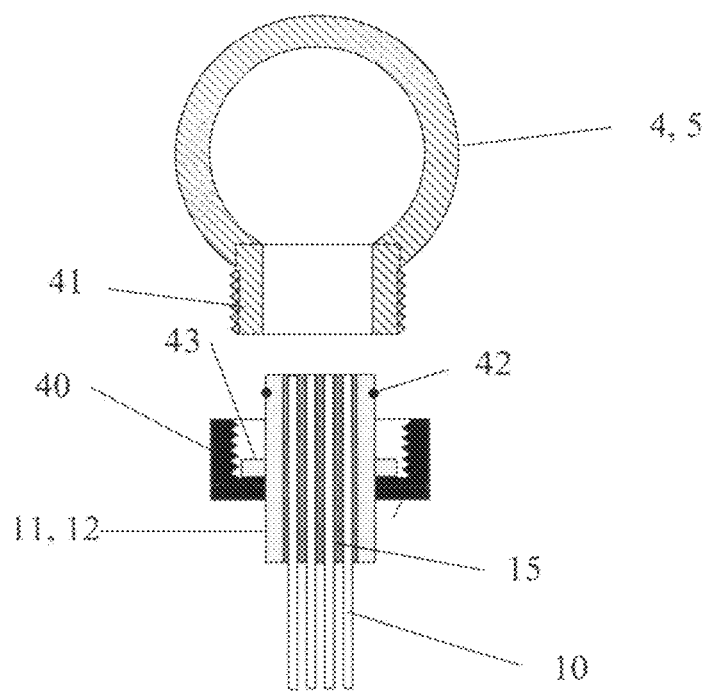
FIG. 5 shows a connection of the tube module heads to the supply element.

FIG. 5 shows by way of example, but not restricting the invention, a fixing possibility with a union nut (40), with which a stop (43) attached to the tube module heads (11), (12) can be drawn against the cylindrical connection piece (41) of the supply lines (4) or (5). This sealing should in this case take place by means of an O-ring (42). Other connections, for example by means of commercially obtainable tube couplings, are also conceivable, as is a simple tube connection between the cylindrical connection pieces (41) and the cylindrical tube module heads (11), (12), which in this case should favorably have the same outside diameter.

Figure 6:
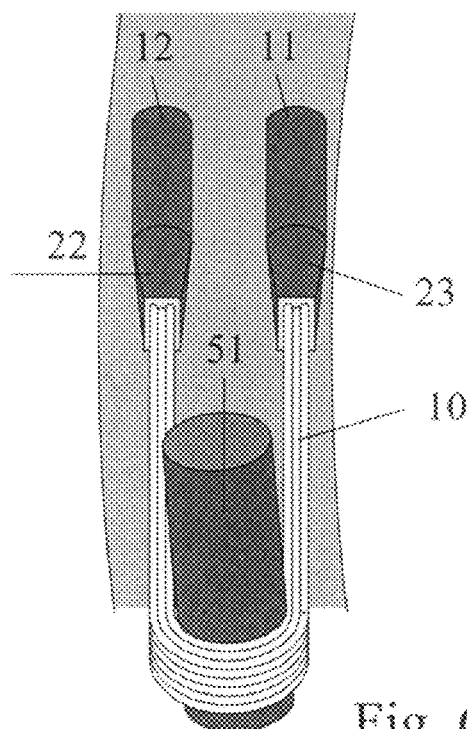
FIG. 6 shows a single-side supply station with opposite deflecting device for the tube membranes.
Figure 7:
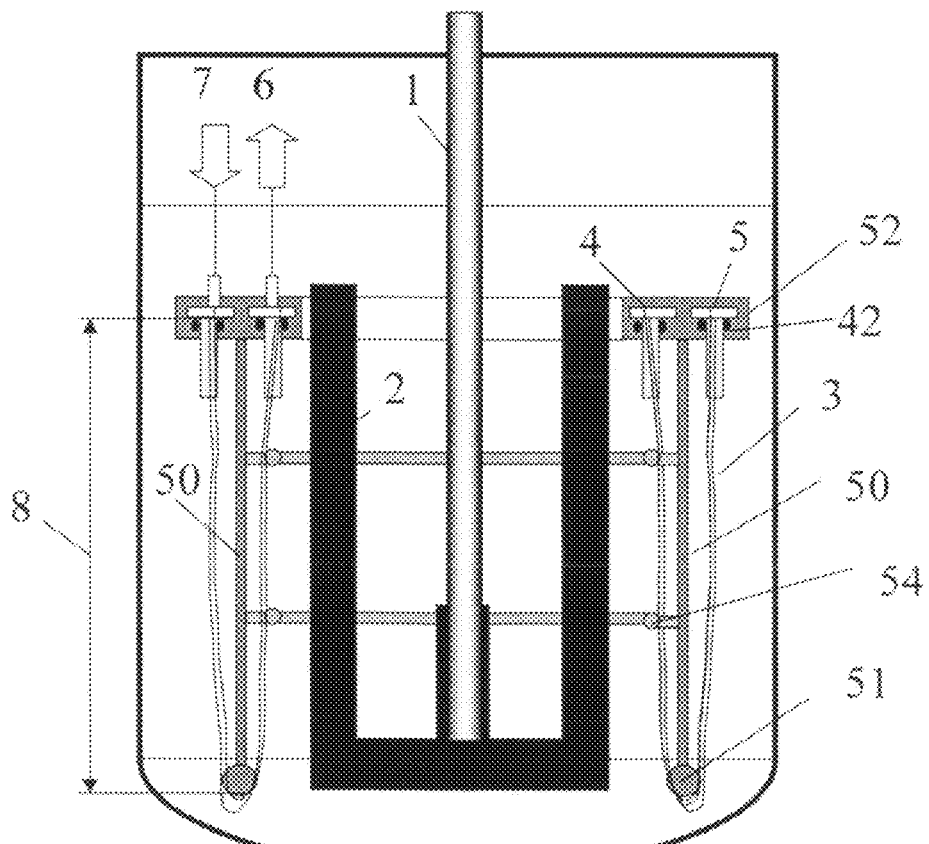
FIG. 7 shows a reactor with a single-side supply station, and a deflecting and protecting device for the tube membranes.

FIGS. 6 and 7 show by way of example, but not restricting the invention, the fixing of the tube modules (3) by means of the tube module heads (11) and (12) to a common supply ring (52), which is equipped with the supply lines (4) and (5) for the gas supply and disposal (6) and (7). In the case of this arrangement, the modules have a tube length that corresponds approximately to twice the stator height (8). An advantage of the arrangement is the increase in the tube surface area in the case of a single-layer modular construction (see FIG. 3) and a reduction in the risk of deposition of the tube module heads (11) restrained in the lower supply line (5) (see FIGS. 2, 3, 4).

In the case of the arrangement of the modules according to FIGS. 6 and 7, the particle discharge takes place in a way analogous to normal vertically wound tube stators, in that the tubes are led around the deflecting ring (51) with one or more layers over half the length of the tube.

In this way, the deflecting ring (51) is connected by means of the connecting elements (50) to the supply ring (52) to form a tube stator. The tube tension can be reduced in the case of this arrangement in such a way as to allow a movement of the tubes in the region of the deflecting ring (51) when they are subjected to flow by the stirrer (2), which distinctly assists particle discharge in comparison with tightly wound stators. In order to prevent the risk of the movable tubes being drawn into the stirring zone, it is necessary to limit the freedom of movement of the tubes by one or more holding rings (54). Depositing of the particles above the supply ring (52) can be brought about in terms of the structural design by installing sliding-off areas or, most simply, as shown in FIG. 6, with stirring blades of the stirrer (2) that are correspondingly extended upward over the supply ring (52), by providing an onflow or overflow.

FIG. 9a, FIG. 9b and FIG. 9c show by way of example, but not restricting the invention, a further possibility for fixing the tube module head (91) to a supply element (90), formed as a matching counterpart, by means of the locking-in elements (93) attached to the module head. After the locking in place, the sealing takes place by the surface pressure of a silicone adhesive compound (15) cast in the module head (91) with a defined height of the surface (92), with which the tubes (10) are at the same time cemented in place in the tube module head (91).

Preferred, particularly preferred or most particularly preferred are embodiments which make use of the parameters, connections, definitions and explanations stated under preferred, particularly preferred or most particularly preferred.

The definitions, parameters, connections and explanations presented in the description as general or presented in preferred ranges may, however, also be combined with one another in any way desired, that is to say between the respective ranges and preferred ranges.

Surprisingly, the aeration of cell culture broths with much higher cell densities than in the case of conventional aeration techniques is possible with the modules according to the invention.

The process engineering advantages of the stators equipped with tube modules as compared with wound stators arise from the use of greatly shortened tube lengths. Since the pressure loss depends on the length to diameter ratio L/D of the tube segment, a proportionate reduction of the tube diameter can be realized by a reduction in length without an increase in pressure loss. A reduction of the tube diameter in turn leads to an increase in the specific tube surface area for the same volume taken up by the tubes in the reactor. A further decisive advantage is the required wall thickness of the tubes, which, in a strength-dependent manner, reduces proportionately with decreasing tube diameter. This results in a reduction in the diffusion resistance in the tube, which limits the oxygenation when membranes are subjected to good flow by the stirring element. A third advantage is the design-dependent higher positive pressure of short pieces of tube, which can be realized over the entire length of the tube, as compared with long wound tubes, in the case of which the difference in pressure between inside the tube and outside the tube that is decisive for the oxygen transfer falls distinctly over the length of the tube. Apart from the improved oxygen transfer into the medium, there is the possibility of selectively improving the $CO_2$ desorption by a second supply network, operated at lower pressures, if required even in the negative pressure range.

The freedom gained by improved mass transfer for oxygen and $CO_2$ can be used for supplying a greater cell density, for increasing the scale and/or for reducing the shearing rate in the reactors as a result of a reduction in the power input. Surprisingly, the very laborious production of a tube stator of 1-2 days can be reduced by the type of construction according to the invention to a duration of a few minutes. In addition, the reproducibility of the tube coverage can be distinctly increased by the use of designated disposable modules as compared with wound tube stators, in the case of which the tube tension cannot be exactly set by the operating personnel.

The tube modules according to the invention are suitable in principle for use in any desired reaction requiring gas to be supplied, but in particular for the aeration of sensitive cell culture broths in biotechnical process engineering, where the particularly gentle aeration according to the present invention can display its full advantages.

The invention claimed is:

1. A tube module, comprising:
    a head mounting;
    a foot mounting; and
    a plurality of tubes aligned in parallel in the head mounting and the foot mounting, the plurality of tubes being configured to be connected by connections to a mounting for regulating the supply and removal of gas,
    wherein inserts of the plurality of tubes within the head mounting and the foot mounting are arranged in vertically stretched single- or multi-layer parallel sheets.

2. The tube module as claimed in claim 1, wherein each of the plurality of tubes has a length of 1-2 times a stator height.

3. The tube module as claimed in claim 1, wherein ends of each tube of the plurality of tubes is fixed in a gas-tight manner in the head and foot mountings.

4. A device, comprising a mounting and at least one associated tube module, as claimed in claim 1.

5. The device as claimed in claim 4, wherein said device is subjected to the flow of a coaxially arranged stirring element.

6. The device as claimed in claim 4, wherein head pieces of the tube module are connected to the mounting by screw connection, by tube connection, by tube coupling or locking-in elements.

7. The device as claimed in claim 4, wherein the mounting is a stator with an opposite deflecting device for supplying gas (gas supply and removal) from above and tube deflection.

8. The device as claimed in claim 4, further including holding devices configured to prevent the tubes from being drawn in by a stirring element.

9. A method of using the device as claimed in claim 4, comprising:
    aerating a liquid media.

10. The tube module as claimed in claim 2, wherein ends of each tube of the plurality of tubes is fixed in a gas-tight manner in the head and foot mountings.

11. A device, comprising a mounting and at least one associated tube module, as claimed in claim 2.

12. A device, comprising a mounting and at least one associated tube module, as claimed in claim 3.

13. The device as claimed in claim 5, wherein head pieces of the tube module are connected to the mounting by screw connection, by tube connection, by tube coupling or locking-in elements.

14. The device as claimed in claim 5, wherein the mounting is a stator with an opposite deflecting device for supplying gas (gas supply and removal) from above and tube deflection.

15. The device as claimed in claim 6, wherein the mounting is a stator with an opposite deflecting device for supplying gas (gas supply and removal) from above and tube deflection.

16. The device as claimed in claim 5, further including holding devices configured to prevent the tubes from being drawn in by the stirring element.

17. The device as claimed in claim 6, further including holding devices configured to prevent the tubes from being drawn in by a stirring element.

18. The method as claimed in claim 9, wherein the liquid media is a cell culture broth.

19. The tube module as claimed in claim 1, wherein the inserts of the plurality of tubes are arranged in vertically stretched single- or multi-layer parallel sheets in at least the head mounting.

20. The tube module as claimed in claim 1, wherein the tube module is configured to be disposable.

* * * * *

UNITED STATES PATENT AND TRADEMARK OFFICE
CERTIFICATE OF CORRECTION

| | | |
|---|---|---|
| PATENT NO. | : 8,328,167 B2 | Page 1 of 1 |
| APPLICATION NO. | : 12/084418 | |
| DATED | : December 11, 2012 | |
| INVENTOR(S) | : Kauling et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1059 days.

Signed and Sealed this
Eleventh Day of November, 2014

Michelle K. Lee
*Deputy Director of the United States Patent and Trademark Office*